(12) United States Patent
Cora et al.

(10) Patent No.: US 8,452,381 B2
(45) Date of Patent: May 28, 2013

(54) GANTRY SYSTEM

(75) Inventors: Sorin V. Cora, Anaheim, CA (US);
Mark E. Desilets, San Jose, CA (US);
Dumitru Dragan, Fremont, CA (US);
Moataz Karmalawy, San Ramon, CA (US); Michael J. Petrillo, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1717 days.

(21) Appl. No.: 11/721,744

(22) PCT Filed: Dec. 5, 2005

(86) PCT No.: PCT/IB2005/054068
§ 371 (c)(1),
(2), (4) Date: Jun. 14, 2007

(87) PCT Pub. No.: WO2006/064402
PCT Pub. Date: Jun. 22, 2006

(65) Prior Publication Data
US 2009/0312634 A1   Dec. 17, 2009

Related U.S. Application Data

(60) Provisional application No. 60/637,294, filed on Dec. 17, 2004.

(51) Int. Cl.
*A61B 6/00* (2006.01)
*G01T 1/164* (2006.01)
*H05G 1/00* (2006.01)

(52) U.S. Cl.
USPC ............... 600/436; 600/407; 600/411; 378/4; 378/17; 378/25; 378/37; 378/38; 378/40; 378/63; 378/204

(58) Field of Classification Search
USPC .. 378/25, 63, 4, 17, 37, 38, 40, 204; 600/407, 600/411, 436
See application file for complete search history.

(56) References Cited

U.S. PATENT DOCUMENTS

| 3,281,598 A | 10/1966 | Hollstein |
| 4,150,297 A | 4/1979 | Borggren |
| 4,649,560 A | 3/1987 | Grady et al. |

(Continued)

FOREIGN PATENT DOCUMENTS

| DE | 19643901 C1 | 4/1997 |
| EP | 0165157 A1 | 12/1985 |

(Continued)

OTHER PUBLICATIONS

Siemens Medical; c.cam—A Whole New Angle in Cardiology; 2003; www.siemens.com/medical.

*Primary Examiner* — Baisakhi Roy

(57) ABSTRACT

A apparatus particularly well suited for use in medical imaging includes radiation sensitive detectors (40, 50) which detect gamma radiation indicative of radionuclide decays in an examination region (30). The detectors (40, 50) are supported by generally c-shaped support (70) for rotation about a detector rotation axis (35). The support (70) is farther attached to a pivot joint (77) which allows adjustment of the detector rotation axis (35). The support (70) may also be translated in two degrees of freedom to so that the detectors (40, 50) orbit the examination region (20) in a non-circular orbit.

20 Claims, 6 Drawing Sheets

U.S. PATENT DOCUMENTS

| | | | |
|---|---|---|---|
| 5,050,204 | A | 9/1991 | Siczek et al. |
| 5,086,447 | A | 2/1992 | Siczek et al. |
| 5,095,501 | A | 3/1992 | Kobayashi |
| 5,327,890 | A | 7/1994 | Matura et al. |
| 5,410,584 | A | 4/1995 | Schaefer et al. |
| 5,444,252 | A | 8/1995 | Hug et al. |
| 5,569,924 | A | 10/1996 | Plummer |
| 5,717,212 | A | 2/1998 | Fulton et al. |
| 5,838,009 | A | 11/1998 | Plummer et al. |
| 6,031,888 | A | 2/2000 | Ivan et al. |
| 6,113,764 | A | 9/2000 | Emch |
| 6,147,353 | A | 11/2000 | Gagnon et al. |
| 6,150,662 | A * | 11/2000 | Hug et al. ............... 250/363.05 |
| 6,158,713 | A | 12/2000 | Ohya et al. |
| 6,294,788 | B1 | 9/2001 | Cooke et al. |
| 6,373,060 | B1 * | 4/2002 | Yamakawa et al. ...... 250/363.08 |
| 6,435,713 | B1 | 8/2002 | Iizuka |
| 6,461,039 | B1 | 10/2002 | Klotz et al. |
| 6,580,777 | B1 * | 6/2003 | Ueki et al. ................ 378/17 |
| 6,619,840 | B2 | 9/2003 | Rasche et al. |
| 7,099,428 | B2 * | 8/2006 | Clinthorne et al. ........... 378/17 |
| 7,489,759 | B2 * | 2/2009 | Beyrard ....................... 378/25 |
| 7,609,808 | B2 * | 10/2009 | Tornai et al. ................ 378/63 |
| 2001/0005410 | A1 | 6/2001 | Rasche et al. |
| 2002/0141532 | A1 | 10/2002 | Koppe et al. |
| 2003/0235265 | A1 * | 12/2003 | Clinthorne et al. ............. 378/4 |
| 2006/0067464 | A1 * | 3/2006 | Clinthorne et al. ............ 378/38 |

FOREIGN PATENT DOCUMENTS

| | | |
|---|---|---|
| EP | 0224886 A1 | 6/1987 |
| EP | 0244596 A1 | 11/1987 |
| JP | 03012136 A | 1/1991 |
| WO | 2004017832 A2 | 3/2004 |

\* cited by examiner

GANTRY SYSTEM

CROSS REFERENCE TO RELATED APPLICATIONS

This application claims the benefit of U.S. provisional application Ser. No. 60/637,294 filed Dec. 17, 2004, which is incorporated herein by reference.

This disclosure relates to the field of nuclear imaging. Specifically, the disclosure relates to devices and methods for positioning radiation detectors used in medical imaging.

Nuclear imaging systems, such as positron emission tomography (PET) systems and single photon emission computed tomography (SPECT) systems generally utilize one or more detectors positioned about a patient for the purpose of collecting data regarding anatomical structures and bodily functions of the patient. Collected data may be used to reconstruct images that clinicians can use for diagnostic purposes.

In single photon imaging, one or more radiation detectors are mounted on a movable gantry to view an examination region that contains a subject to be imaged. The subject is typically a patient that is a human or laboratory animal. Commonly, one or more radiopharmaceuticals capable of generating emission radiation are injected into the subject. The radiopharmaceutical preferably travels to an organ of interest within the subject that a clinician desires to examine. The detector(s) scan the subject along a selected path or scanning trajectory and radiation events are detected by the detector(s).

A typical detector includes a collimator and a scintillation crystal that is viewed by an array of photomultiplier tubes. Relative outputs of the photomultiplier tubes are typically processed and corrected to generate an output signal that indicates first, a position coordinate on the detector at which each radiation event is detected and second, an energy of each event. The energy of the event is used to differentiate among various types of radiation such as multiple radiation emission sources, stray radiation, secondary radiation, transmission radiation, and sources of noise. The radiation data is then reconstructed into an image representation of a region of interest.

In positron emission imaging, annihilation events result in the emission of a pair of photons with a particular energy level. The emitted photons travel in opposite directions from the annihilation site. Typically, positron emission detectors are deployed in diametrically opposed pairs with a radiation-receiving face of each detector facing the other detector. A photon detected by the first detector in the pair is matched with a photon detected by the second detector of the pair based upon a variety of indicating factors. The system then derives a line of flight based upon the relative positions of the detected photons and uses that information to reconstruct an image representation of a region of interest.

The preferred detector configuration is often a function of the type of examination being performed. For example, cardiac imaging systems often use two detectors that are orthogonally positioned relative to each other. This orientation enables a complete 180 degree data set to be collected by rotating the pair of detectors only ninety degrees (90°) about the subject. It is desirable to have the radiation-receiving face of the detector(s) as close to the subject as possible during a diagnostic scan for collimated imaging to minimize any loss in spatial resolution due to collimator blur. Consequently, there is a need for a gantry system that positions the detector(s) as close a possible to the subject. Additionally, a clinician may desire to position a subject in various orientations for various reasons, including access to a region of interest in the subject or the comfort of the subject during examination.

Therefore, there is a need for a gantry system that provides for a range of positioning options.

Aspects of the present application address these matters, and others.

According to a first aspect of the present invention, an apparatus includes a first radiation sensitive detector which detects gamma radiation indicative of radionuclide decays in an examination region and a gantry which movably supports the detector in relation to the examination region. The first detector is selectively translatable and rotatable about the examination region for movement in a noncircular orbit, and the plane of the orbit is adjustable between at least first and second orientations.

According to a more limited aspect of the present invention, the examination region is adapted to receive a human patient. The plane of the orbit is adjustable between a first position in which the plane of the orbit is substantially orthogonal to the longitudinal axis of a patient in a reclining position and a second position in which the plane of the orbit is substantially orthogonal to the longitudinal axis of a patient in at least one of a seated or a recumbent position.

According to a still more limited aspect of the present invention, the plane of the orbit is adjustable over a range of 90 degrees.

According to another more limited aspect of the present invention, the apparatus includes a first support and an arcuate support. The arcuate support supports the first detector for rotation about a detector rotation axis. Thee arcuate support is operatively connected to the first support for pivotal motion about a pivot axis so that pivoting the arcuate support adjusts the plane of the orbit.

According to a still further limited aspect of the invention, the pivot axis is perpendicular to the detector rotation axis.

According to a still further limited aspect, the first support is translatable in a first direction parallel to the pivot axis. The first support is also translatable in a second direction perpendicular to the pivot axis.

According to a still further limited aspect, the apparatus includes a vertical drive operatively connected to the first support. The vertical drive selectively translates the first support in a vertical direction. The apparatus also includes a horizontal drive operatively connected to the first support. The horizontal drive selectively translates the first support in a horizontal direction.

According to another more limited aspect of the present invention, the apparatus includes a second arcuate support. The first detector is fixedly mounted to the second support. The second arcuate support is operatively connected to the first arcuate support for rotation about the detector rotation axis.

According to another more limited aspect, the apparatus also include a curved rack and pinion which is operatively connected to the first and second arcuate supports.

According to yet another more limited aspect of the present invention, the apparatus includes a second radiation sensitive detector which detects gamma radiation indicative of radiation decays in the examination region. The arcuate support supports the second detector for rotation about the detector rotation axis. The first detector and second detectors are disposed in a perpendicular configuration.

According to more limited aspect of the present invention, the apparatus includes an image reconstruction system operatively connected to the first detector and a drive system for selectively controlling translation and rotation of the first detector.

According to still more limited aspect, the orbit is substantially elliptical.

The apparatus may also include a plurality of radiation sensitive detectors disposed in an arc about the examination region, for example three detectors disposed in a 60 degree configuration.

According to another aspect of the present invention, an apparatus includes a first support, a generally c-shaped support, a pivot joint, and first and second radiation sensitive detectors which detect gamma radiation indicative of radionuclide decays occurring in an examination region. The pivot joint has a horizontal pivot axis and is operatively connected to the c-shaped support and the first support. The first and second detectors are disposed in a perpendicular configuration and operatively connected to the generally c-shaped support for rotation about a detector rotation axis. The detector rotation axis is perpendicular to the pivot axis. The c-shaped support is pivotable between a first position in which the detector rotation axis is parallel to the longitudinal axis of a human subject disposed in the examination region in a reclining position and a second position wherein the detector rotation axis is parallel to the longitudinal axis of a human subject disposed in the examination region in one of a recumbent or a vertical position.

According to a more limited aspect of the invention, the c-shaped support is pivotable over a range which includes a first position which the detector rotation axis is horizontal and a second position wherein the detector rotation axis is vertical.

According to a still more limited aspect, the apparatus may also include a drive which causes the detectors to rotate about the detector rotation axis, a drive which translates the first support in a direction parallel to the pivot axis, and a drive which translates the first support in a vertical direction.

According to still more limited aspect of the present invention, the apparatus includes a control system which coordinates the movement of the drives so that the detectors travel about the examination region in a non-circular orbit.

The orbit may be substantially elliptical and have a range of approximately 90 degrees.

According to another more limited aspect, the apparatus may be adapted for floor mounting.

The apparatus may also include a second c-shaped support in which the first and second detectors are supported by the second c-shaped support for movement therewith. The drive which causes the detectors to rotate about the detector rotation axis includes curved a rack and pinion operatively connected to the first c-shaped support and the second c-shaped support.

According to another more limited aspect of the present invention, the apparatus includes a subject support adapted to support the subject in a reclining position and at least one of a recumbent and a seated position.

Still other aspect of the present invention will be appreciated by those skilled in the art upon reading and understanding the attached description.

Figure 1A:
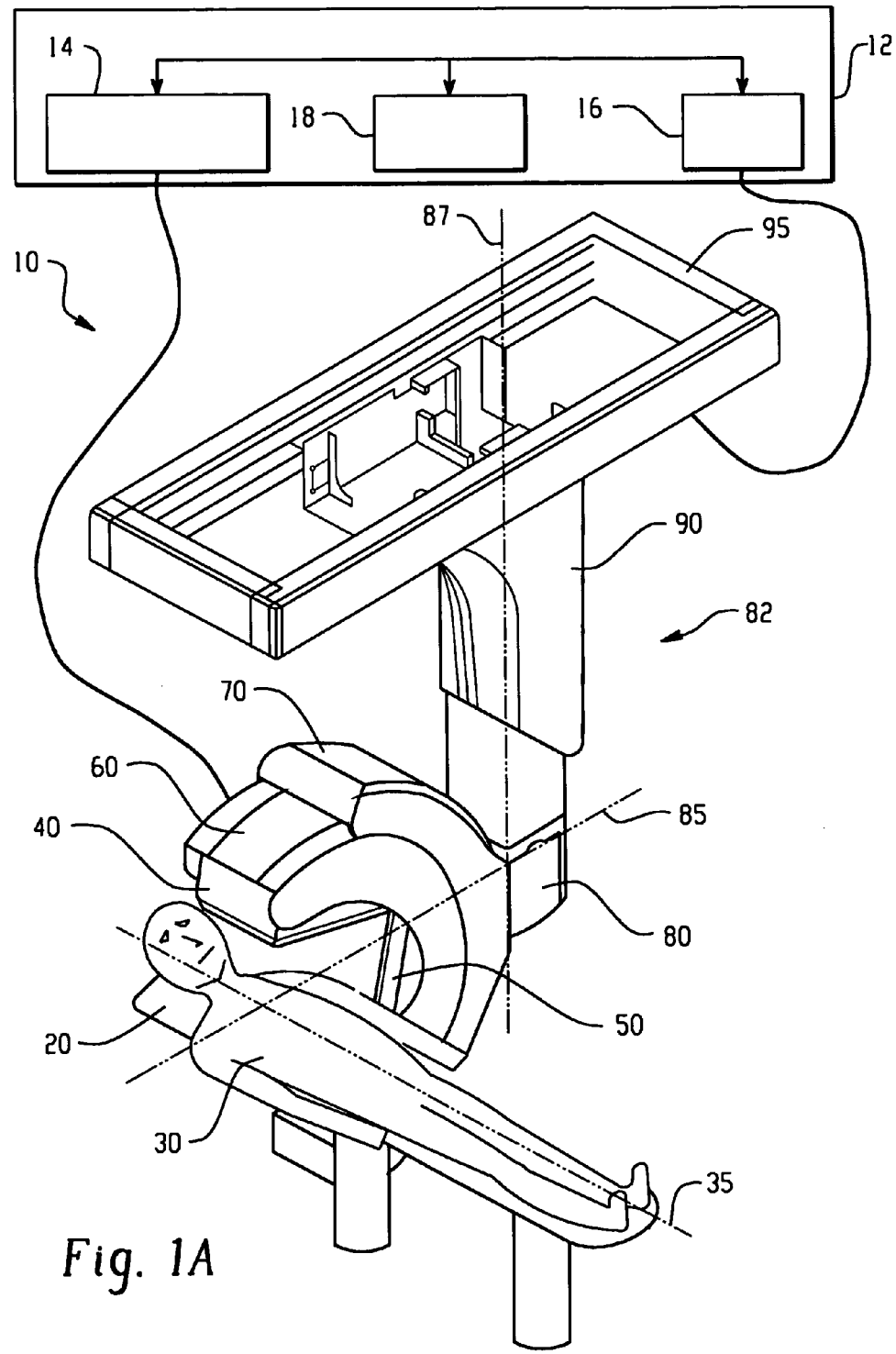
FIG. 1A is a perspective illustration of an overhead-supported medical imaging system.

With reference to FIG. 1A, an imaging system includes a gantry 10, a patient support 20, and an imaging system 12.

The gantry 10 supports first and second radiation sensitive detectors 40, 50 which detect radiation indicative of radionuclide decays occurring within an examination region 30.

The detectors 40, 50 are mounted to an arcuate detector support 60 so that they face the examination region in a perpendicular configuration. Such a perpendicular configuration is not limited to precisely 90 degrees, and other perpendicular configurations (e.g., a 102 degree configuration) may also be implemented depending on the particular imaging application.

Figure 1B:
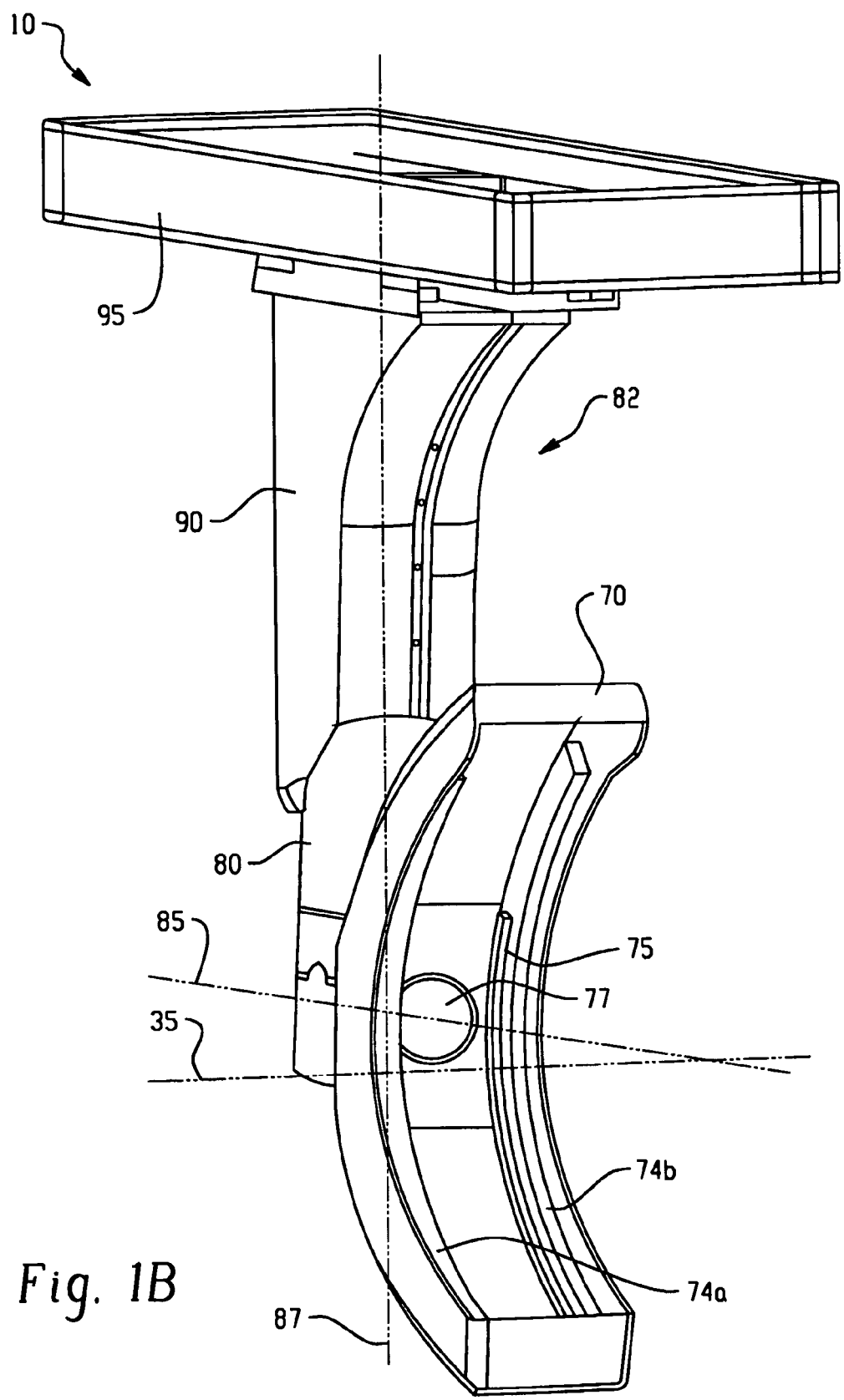
FIG. 1B is a perspective view of a detector support carrieran illustration of a gantry.

With reference to FIGS. 1A and 1B, the detector support 60 is in turn movably mounted to a detector support carrier 70 for rotation about a detector rotation axis 35 using a drive such as a classic curved rack and pinion mechanism. The carrier 70 includes circular guides 74a, 74b along which the detector support 60 can slide.

A motor driven pinion is attached to the detector support 60. The pinion engages a curved rack 75 disposed on the carrier 70 to drive the detector support 60 along the curved guides 74a, 74b when the motor is powered. Suitable alternatives to a rack and pinion system may be also used.

In order to collect the data needed to generate a SPECT image, the perpendicular detectors 40, 50 travel along an arc of approximately 90 degrees or approximately one-quarter of a full revolution about the axis 35. Of course, other angular ranges may also be implemented.

With continuing reference to FIGS. 1A and 1B, the gantry 10 also includes a support 82 which includes a movable telescoping portion 80 and a stationary telescoping portion 90. The carrier 70 is mounted to the movable portion 80 via a pivot joint 77 for pivotal motion about a pivot axis 85. The pivot axis 85 is perpendicular to the detector rotation axis 35. The pivot joint 77 preferably allows the angular position of the carrier 70 to be adjusted over a range of approximately 90 degrees such that the detector rotation axis 35 may be visualized as ranging between the horizontal (as shown) and vertical positions. Stated another way, the detectors 40, 50 may be viewed as orbiting the examination region in a plane which varies between the vertical (as shown) and horizontal positions. Of course, angular ranges greater or lesser than 90 degrees may also be implemented.

The user or operator manually positions the carrier 70 and hence the detectors 40, 50 about the pivot joint 77. A locking mechanism allows the user to lock the pivot joint 77 in position when carrier 70 is in the desired angular position. The pivot joint 77 may also include one or more detents which facilitate positioning the carrier 70 in a defined angular position. Alternately, a drive such as an electric motor can be used to cause pivotal motion of the carrier 70 about the pivot joint 77. A combination of motor drive and manual movement may also be implemented.

As shown, the support 82 is implemented as a substantially vertical telescoping arm, the length of which is adjustable along an axis 87 which is perpendicular to the pivot axis 85. A drive such as an electrical motor coupled to suitable gearing causes translational motion of the support 80 along the axis 87.

The support 82 is in turn movably mounted to a fixed frame 95 for linear movement in the direction of the pivot axis 85. In the illustrated embodiment, the fixed frame 95 is attached to a ceiling or other suitable overhead support. Alternately, the fixed frame may be attached to the floor, wall or other support.

A drive such as an electric motor coupled to suitable gearing causes translational motion of the support 90 along the direction of the pivot axis 85. Alternatively, the operator or user may position the support 90 manually. A combination of motor drive and manual movement may also be implemented.

The details of such an overhead support system are described in U.S. Pat. No. 6,150,662 to Hug, et al. which is expressly incorporated herein by reference.

The patient support 20 supports an object to be imaged, for example a human patient, in the examination region 30. As illustrated, the support 20 takes the form of a patient couch or bed wherein the patient's torso is disposed in a substantially horizontal position. Alternatively, support 20 may include a chair or seat which facilitates the positioning of the patient's torso in a position other than horizontal, for example in a substantially vertical or a reclining position. Moreover, the patient support 20 may be adjustable or reclinable to facilitate positioning in more than one of such positions. The patient support 20 may also be omitted, especially where it is desirable that the patient be positioned in a standing position.

The imaging system 12 includes a reconstruction system 14, a gantry control system 16, and an operator interface 18. The reconstruction system 14 processes the signals from the detectors 40, 50, to reconstruct an image indicative of the detected radiation as is conventional in the art. The gantry controller 16 controls the drivers associated with the various joints in the gantry so that the detectors 40, 50 orbit the examination region and patient in a desired trajectory. The operator interface 18 displays the generated images in human readable form, for example on a monitor, film, or printer. The data may also be stored in electronic form and transmitted over a communication network for reconstruction and/or viewing at a remote location. The operator interface 18 also accepts operator input for specifying scan protocols and otherwise controlling system operation.

Figure 2A:
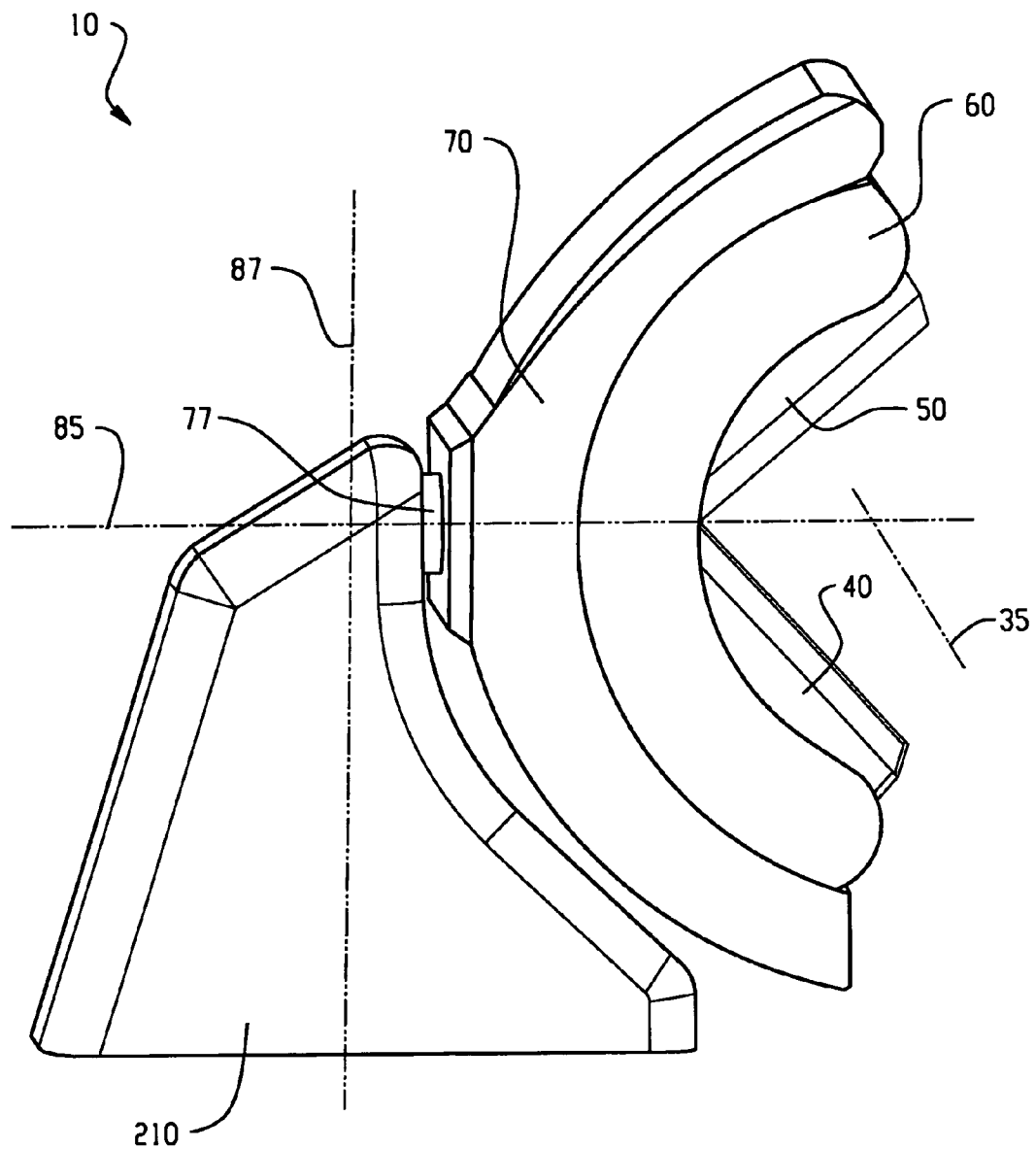
FIG. 2A is an second perspective illustration of the a gantry and detector assembly with detectors.
Figure 2B:
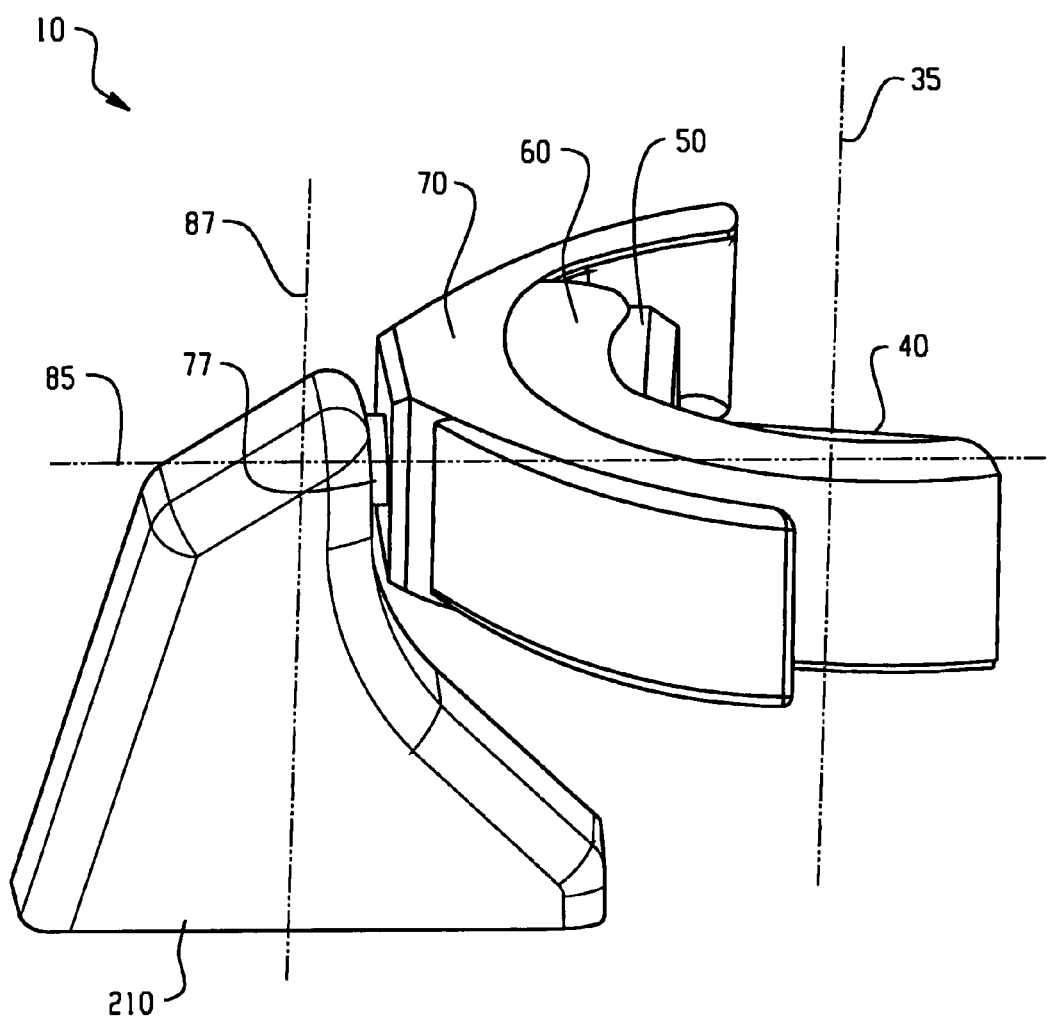
FIG. 2B is an third perspective illustration of the a gantry and with detectors assembly.
Figure 2C:
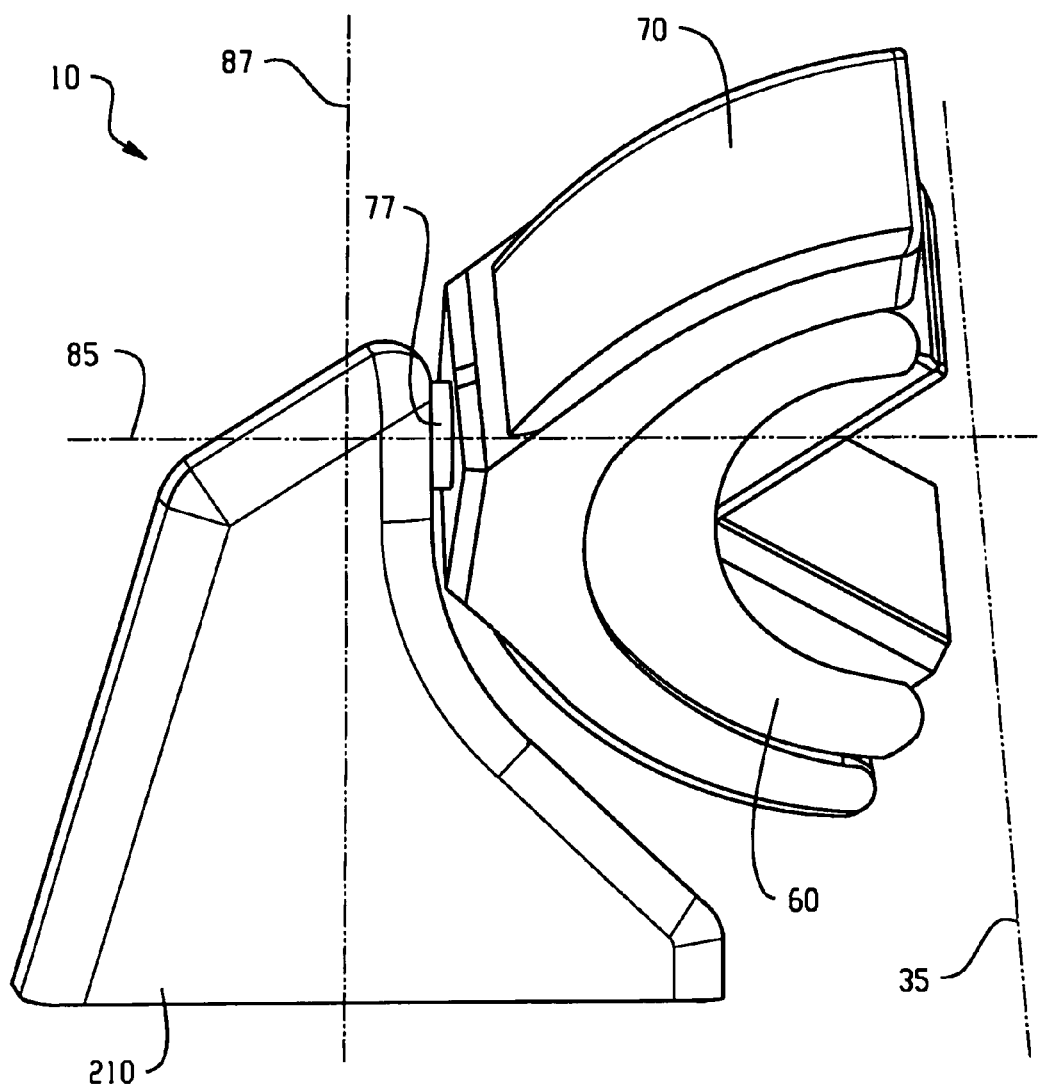
FIG. 2C is an fourth perspective illustration of the a gantry and with detectors assembly.

FIGS. 2A, 2B, and 2C depict an alternate embodiment of the gantry 10. As described above in relation to FIGS. 1A and 1B, the gantry 10 includes first 40 and second 50 radiation sensitive detectors, a detector support 60, a detector support carrier 70 and associated drive mechanism, and a pivot joint 77. Also as described above, the detectors 40, 50 are rotatable about the detector rotation axis 35. Likewise, the carrier 70 and thus the detectors 40, 50 pivot about the pivot axis 85.

Pivot joint 77 is movably mounted to the base mount 210 for translation along vertical axis 87. Similarly, the base mount 210 is movably mounted to the floor or other support for translatable movement in a direction parallel to pivot axis 85. Suitable linear drivers such as a straight rack and pinion or lead screw systems, in cooperation with appropriate linear guides can be used to generate these required movements.

FIG. 2A shows the gantry 10 with the carrier 70 positioned so that the detector rotation axis 35 is substantially horizontal. Stated another way, the detectors 40, 50 orbit the examination region in a plane which is substantially vertical. FIG. 2B shows the gantry 10 with the carrier 70 rotated about the pivot joint by 90 degrees so that the detector rotation axis 35 is substantially vertical. Stated another way, the detectors 40, 50 orbit the examination region in a plane which is substantially horizontal. FIG. 2C shows the gantry 10 with the carrier 70 rotated about the pivot joint so that the detector rotation axis 35 is about 45 degrees from the vertical. Stated another way, the detectors 40, 50 orbit the examination region in a plane which is about 45 degrees from the horizontal.

Figure 2D:
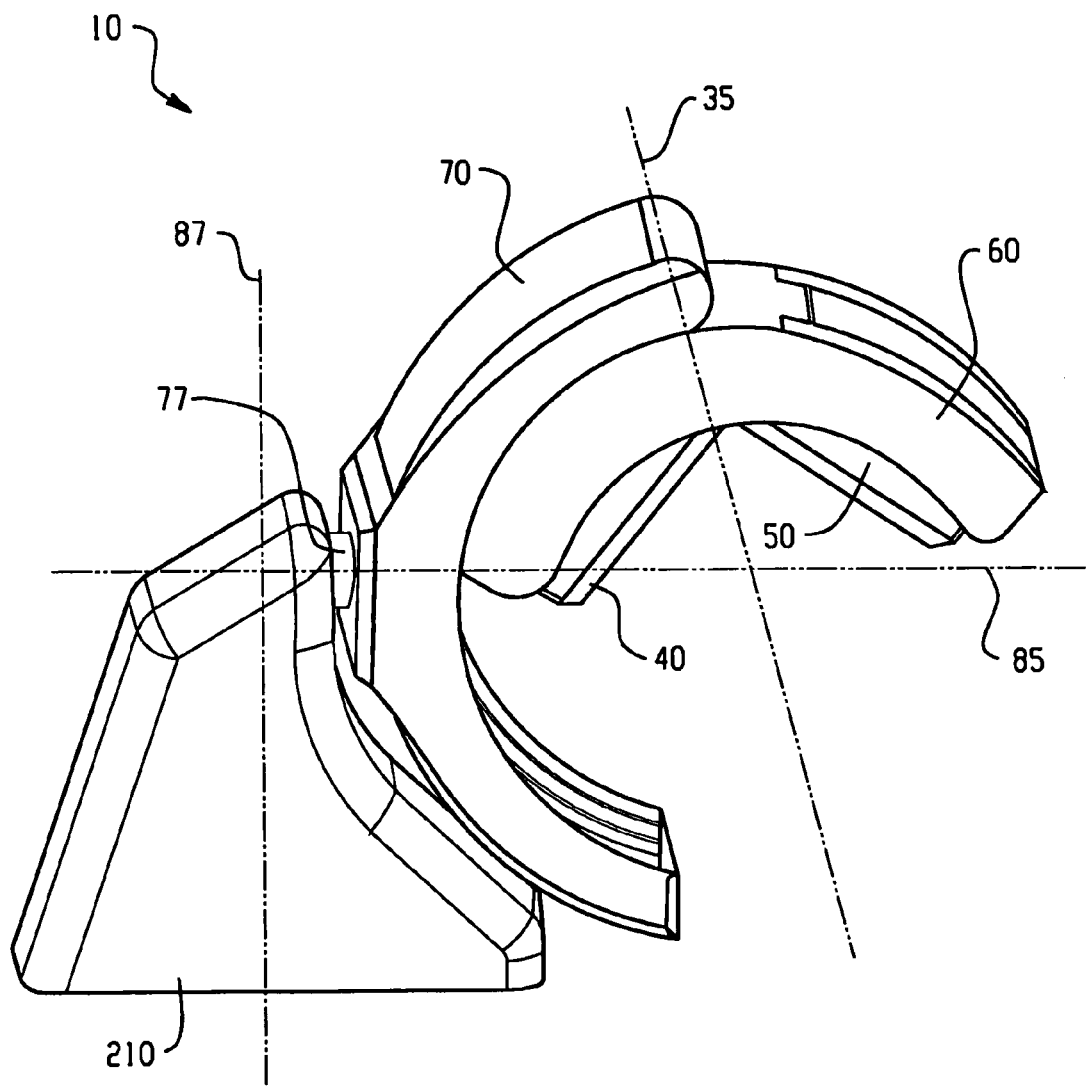
FIG. 2D is an illustration of gantry with detectors.

FIG. 2D shows gantry 10 with the detector support 60 and thus the detectors 40, 50 rotated about the detector rotation axis 35 by approximately 90 degrees compared to FIG. 2A. In both figures, the detector rotation axis 35 is depicted as being oriented horizontally. As will be appreciated, rotating the first 40 and second 50 detectors by 90 degrees during data collection results in the acquisition of a complete SPECT data set. As will also be appreciated, similar rotations of the detector support 60 and thus the detectors 40, 50 may be accomplished with the detector rotation axis 35 oriented in other positions, for example in the positions shown in FIGS. 2B and 2C.

In operation, the patient or other object being imaged is positioned on the support 20 in a desired position. The operator positions the detectors 40, 50 by pivoting the detector support carrier 70 about the pivot axis 85 until the detector rotation axis 35 is suitably positioned.

In cardiac imaging, for example, it is often advantageous to position the patient in a seated position wherein the torso or longitudinal axis of the patient is positioned along a substantially vertical axis. In this case, the operator pivots the carrier 70 so that the detector rotation axis 35 is substantially vertical. Stated another way, the operator pivots the carrier 70 so that the plane of the orbit traced by detectors 40, 50 is substantially horizontal. In other applications, it may be advantageous to position the patient in a recumbent positions such as a prone or supine position wherein the torso of the patient is positioned along a substantially horizontal axis. In this case, the operator pivots the carrier 70 so that the detector rotation axis 35 is substantially horizontal. Stated another way, the operator pivots the carrier 70 so that the plane of the orbit traced by detectors 40, 50 is substantially vertical. In still other applications, it may be desirable to position the patient so he or she is neither lying or seated, such as in a reclining position where the torso of the patient is at an angle to the vertical. In this case, the operator pivots the carrier 70 so that the detector rotation axis 35 is at a corresponding angle to the vertical. Stated another way, the operator pivots the carrier 70 so that the plane of the orbit traced by detectors 40, 50 is at an angle to the vertical. In each case, the operator pivots the carrier 70 so that the detector rotation axis 35 is substantially parallel to the of the patient's longitudinal axis. Stated another way, the operator pivots the carrier 70 so that the orbit traced by detectors 40, 50 is in a plane which is substantially orthogonal to the torso of the patient.

In still other applications, for example imaging the heart, liver, bladder or other internal organs, it may be desirable to pivot the carrier 70 so that the detector rotation axis 85 does not align with the torso of the patient. Positioning the carrier 70 in this way facilitates the collection of an oblique data set, for example one which is in a caudal or cephalic relation to the patient.

In any case, once the carrier 70 is in the desired position, the operator locks the pivot joint 77 in place.

The operator also uses the operator interface to specify the imaging protocol and to position the translational drives along the pivot axis 85 and axis 87 so that the carrier 70 is positioned in a default or initial position with respect to the patient. During imaging, the detectors 40, 50 detect gamma radiation indicative of radionuclide decays occurring in the examination region 30. The gantry control system 16 coordinates rotation of the detectors 40, 50 about the detector rotation axis 35 and the translational movements along the pivot 85 and vertical axes 87 so that the detectors 40, 50 trace a desired orbit about the patient. In one such orbit, the detectors 40, 50 trace a substantially elliptical orbit wherein the detectors 40, 50 are positioned as close as possible to the body of the patient. Stated another way, the gantry control system 16 coordinates rotation of the detectors 40, 50 about the detector rotation axis 35 and the translational movements of the carrier 70 and thus the detector rotation axis 35 so that the detectors travel in the desired orbit. It should be noted that it is not necessary that the detectors 40, 50 travel in a complete 360 degree orbit about the examination region. In the two detector embodiment described in FIGS. 1 and 2, for example, the detectors 40, 50 each orbit along an arc of approximately 90 degrees. It should also be noted that, in the illustrated embodiments, it is possible to generate elliptical orbits suitable for human imaging with only relatively small translational movements.

The image reconstruction system 14 uses the data collected by the detectors 40, 50 to generate an image indicative of the radionuclide decays. The images are provided to the operator via the operator interface 18.

The system was described above as including first 40 and second 50 radiation sensitive detectors disposed perpendicularly facing the examination region 30. Alternatively, the system may include a single radiation sensitive detector. In this case, the detector support 60, the carrier 70, and the associated drive are preferably modified to allow the detector to rotate or orbit through an arc of approximately 180 degrees to collect a complete SPECT data set. The system may also include three detectors in an angular relationship of 60 degrees to each other. More generally, the system may include additional detectors spaced angularly about the imaging retion In each case, the range of rotation may be suitably modified.

Although the system has been described in relation to conventional scintillator/photomultiplier tube detectors, other detector technologies can also be used. For example, alternate photosensors can be used, as can semiconductor or other detectors which convert incident radiation directly to electrical energy. Moreover, the system can be implemented using curved detectors which subtend a portion of the arc about the patient. It should also be noted the gantry can be used with suitable detectors and coincidence logic for operation with positron emission tomography (PET) systems.

The invention has been described with reference to the preferred embodiments. Obviously, modifications and alterations will occur to others upon reading and understanding the preceding description. It is intended that the invention be construed as including all such modifications an alterations insofar as they come within the scope of the appended claims or the equivalents thereof.

The invention claimed is:

1. An apparatus comprising:
   a first support which is mounted for translation relative to an examination region;
   a second support which defines an arcuate track, the second support being operatively connected to the first support;
   a pivot construction which enables the second support to pivot relative to the first support around a pivot axis to define an orbital plane;
   first and second radiation sensitive detectors which detect gamma radiation indicative of radionuclide decays in an examination region, the first and second detectors being movably supported by the arcuate track for movement therealong relative to the second support;
   a drive assembly which coordinately moves the detectors along the arcuate track and the second support to move the detectors in a non-circular path in the orbital plane defined by the pivot construction.

2. The apparatus of claim 1, wherein the examination region is adapted to receive a human patient and wherein the orbital plane is adjustable between a first position in which the orbital plane is substantially orthogonal to a longitudinal axis of a patient in a reclining position and a second position in which the orbital plane is substantially orthogonal to the longitudinal axis of a patient in at least one of a seated or a recumbent position.

3. The apparatus of claim 1, further comprising:
   a vertical drive operatively connected to the first support which selectively translates the first support in a vertical direction; and
   a horizontal drive operatively connected to the first support which selectively translates the first support in a horizontal direction.

4. The apparatus of claim 1 further comprising:
   a third support, wherein the first and second detectors are fixedly mounted to the third support, the third support being operatively connected to the second support for movement along the arcuate track.

5. The apparatus of claim 1 wherein the first detector and second detector are disposed in a fixed perpendicular configuration.

6. The apparatus of claim 1, further comprising:
   an image reconstruction system operatively connected to the first and second detectors.

7. The apparatus of claim 1, wherein the orbit is elliptical.

8. The apparatus of claim 1, further comprising a third detector, the first, second, and third detectors being disposed in a 60 degree configuration.

9. The apparatus of claim 1, wherein the drive assembly includes:
   a first drive which moves the detectors along the second support such that the detectors move around the longitudinal axis of the subject;
   a second drive which translates the first support in a direction parallel to the orbital plane; and
   a control system which controls the first and second drives in coordination to move the detectors in the iron-circular path.

10. An apparatus comprising:
    a first support which is mounted for translation relative to an examination region adapted to receive a human patient;
    a second support which defines an arcuate path, the second support being operatively connected to the first support;
    a pivot construction which enables the second support to pivot relative to the first support around a pivot axis to define an orbital plane, the orbital plane being adjustable between a first position in which the orbital plane is substantially orthogonal to a longitudinal axis of a patient in a reclining position and a second position in which the orbital plane is substantially orthogonal to the longitudinal axis of a patient in at least one of a seated or a recumbent position, the pivot axis being perpendicular to the longitudinal axis of the patient;
    first and second radiation sensitive detectors which detect gamma radiation indicative of radionuclide decays in an examination region, the first and second detectors being supported by the second support for movement relative to the second structure along the arcuate path;
    a drive assembly which drives the detectors along the arcuate path and translates the first support to move the detectors in a non-circular path in the orbital plane defined by the pivot construction.

11. The apparatus of claim 10, wherein the orbital plane is adjustable over a range of 90 degrees.

12. The apparatus of claim 10 wherein the first support is translatable in a first direction parallel to the pivot axis and in a second direction perpendicular to the pivot axis.

13. The apparatus of claim 10, wherein the second support includes an arcuate guide track and the drive assembly moves the detectors along the arcuate drive track.

14. An apparatus comprising:
    a first support which is mounted for translation relative to an examination region;
    a second support which defines an arcuate track, the second support being operatively connected to the first support;

a pivot construction which enables the second support to pivot relative to the first support around a pivot axis to define an orbital plane;

first and second radiation sensitive detectors which detect gamma radiation indicative of radionuclide decays in an examination region, the first and second detectors being movably supported by the arcuate track for movement therealong relative to the second support;

a drive assembly which drives the detectors along the arcuate track and translates the first support to move the detectors in a non-circular path in the orbital plane defined by the pivot construction;

a third support, wherein the first and second detectors are fixedly mounted to the third support, the third support being operatively connected to the second support for movement along the arcuate track;

a curved rack and pinion which operatively connects the second and third supports.

15. An apparatus comprising;

a first support;

a generally C-shaped support;

a pivot joint having a horizontal pivot axis and operatively connected to the c-shaped support and the first support;

first and second radiation sensitive detectors which detect gamma radiation indicative of radionuclide decays occurring in an examination region, the first and second detectors disposed in a fixed perpendicular configuration and operatively connected to the generally C-shaped support for rotation about a detector rotation axis, the detector rotation axis being perpendicular to the pivot axis;

wherein the C-shaped support is pivotable between a first position in which the detector rotation axis is parallel to the longitudinal axis of a human subject disposed in the examination region in a horizontal reclining position and a second position wherein the detector rotation axis is parallel to the longitudinal axis of a human subject disposed in the examination region in one of a recumbent or a vertical position;

a first drive which moves the detectors along the C-shaped support such that the detectors move around the longitudinal axis of the subject;

a second drive which translates the first support in a horizontal direction; and a control system configured for coordinating movement of the first and second drives so that the detectors travel about the examination region in a non-circular orbit when the C-shaped support is in the second position.

16. The apparatus of claim 15, wherein the second support is pivotable over a range which includes a first position in which the detector rotation axis is horizontal and a second position wherein the detector rotation axis is vertical.

17. The apparatus of claim 15 wherein the orbit is elliptical and has a range of approximately 90 degrees.

18. The apparatus of claim 15, wherein the apparatus is adapted for floor mounting.

19. The apparatus of claim 15, further comprising a second c-shaped support, wherein the first and second detectors are supported by the second c-shaped support for movement therewith, and wherein the drive which causes the detectors to rotate about the detector rotation axis includes curved a rack and pinion operatively connected to the first e-shaped support and the second c-shaped support, such that the second c-shaped supports moves in an arcuate path along the first c-shaped support.

20. The apparatus of claim 15, further comprising:

a subject support which supports the subject in a reclining position and a second position including at least one of a recumbent and a seated position and wherein the c-shaped support is pivoted to be in a first plane of rotation, perpendicular to the longitudinal axis of the subject when the detectors rotate around the subject in the reclining position and pivoted to and held fixed in a second plane of rotation perpendicular to the longitudinal axis of the subject in the second position when the detectors rotate around the subject in the second position.

* * * * *